(12) United States Patent
Junnarkar et al.

(10) Patent No.: US 11,083,796 B2
(45) Date of Patent: Aug. 10, 2021

(54) PEROXIDE REMOVAL FROM DRUG DELIVERY VEHICLE

(71) Applicant: Durect Corporation, Cupertino, CA (US)

(72) Inventors: Gunjan Junnarkar, Palo Alto, CA (US); Michael A. Desjardin, Aptos, CA (US); John P. Carr, Sunnyvale, CA (US)

(73) Assignee: Durect Corporation, Cupertino, CA (US)

( * ) Notice: Subject to any disclaimer, the term of this patent is extended or adjusted under 35 U.S.C. 154(b) by 0 days.

(21) Appl. No.: 16/542,230

(22) Filed: Aug. 15, 2019

(65) Prior Publication Data

US 2019/0365900 A1 Dec. 5, 2019

Related U.S. Application Data

(63) Continuation of application No. 15/250,822, filed on Aug. 29, 2016, now abandoned, which is a continuation of application No. 13/301,727, filed on Nov. 21, 2011, now abandoned, which is a continuation of application No. 11/492,153, filed on Jul. 24, 2006, now abandoned.

(60) Provisional application No. 60/702,546, filed on Jul. 26, 2005.

(51) Int. Cl.
| | |
|---|---|
| *A61K 47/26* | (2006.01) |
| *A61K 31/7024* | (2006.01) |
| *A61K 9/00* | (2006.01) |
| *A61K 9/10* | (2006.01) |
| *A61K 38/21* | (2006.01) |
| *C07H 1/06* | (2006.01) |
| *C07H 13/04* | (2006.01) |

(52) U.S. Cl.
CPC ............ *A61K 47/26* (2013.01); *A61K 9/0004* (2013.01); *A61K 9/0024* (2013.01); *A61K 9/10* (2013.01); *A61K 31/7024* (2013.01); *A61K 38/21* (2013.01); *C07H 1/06* (2013.01); *C07H 13/04* (2013.01)

(58) Field of Classification Search
CPC .. A61K 9/0024; A61K 47/26; A61K 31/7024; A61K 9/10
USPC .......................................................... 514/54
See application file for complete search history.

(56) References Cited

U.S. PATENT DOCUMENTS

| | | | |
|---|---|---|---|
| 2,931,802 A | 4/1960 | Toney | |
| 3,215,137 A | 11/1965 | Laakso et al. | |
| 3,346,381 A | 10/1967 | Grieg | |
| 3,473,949 A | 10/1969 | Eldred et al. | |
| 3,743,398 A | 7/1973 | Johnson et al. | |
| 3,755,466 A | 8/1973 | Reuter et al. | |
| 3,763,018 A * | 10/1973 | Raff | C07C 7/20 203/9 |
| 3,797,492 A | 3/1974 | Place | |
| 3,853,837 A | 12/1974 | Fujino et al. | |
| 3,962,162 A | 6/1976 | Sclunank | |
| 3,987,790 A | 10/1976 | Eckenhoff et al. | |
| 3,992,365 A | 11/1976 | Beddell et al. | |
| 4,008,719 A | 2/1977 | Theeuwes et al. | |
| 4,024,248 A | 5/1977 | Konig et al. | |
| 4,069,251 A | 1/1978 | Mannsfield et al. | |
| 4,100,274 A | 7/1978 | Dutta et al. | |
| 4,304,767 A | 12/1981 | Heller et al. | |
| 4,305,927 A | 12/1981 | Theeuwes et al. | |
| 4,395,405 A | 7/1983 | Noda et al. | |
| 4,395,495 A | 7/1983 | Cununings | |
| 4,411,890 A | 10/1983 | Momany | |
| 4,487,603 A | 12/1984 | Harris | |
| 4,530,840 A | 7/1985 | Tice et al. | |
| 4,562,024 A | 12/1985 | Rogerson | |
| 4,622,219 A | 11/1986 | Haynes | |
| 4,630,019 A | 12/1986 | Portner et al. | |
| 4,692,147 A | 9/1987 | Duggan | |
| 4,725,442 A | 2/1988 | Haynes | |
| 4,725,852 A | 2/1988 | Gamblin et al. | |
| 4,767,628 A | 8/1988 | Hutchinson | |
| 4,782,104 A | 11/1988 | Nakanishi | |
| 4,795,641 A | 1/1989 | Kashdan | |
| 4,834,984 A | 5/1989 | Goldie et al. | |
| 4,844,909 A | 7/1989 | Goldie et al. | |
| 4,861,598 A | 8/1989 | Oshlack | |
| 4,865,845 A | 9/1989 | Eckenhoff et al. | |
| 4,874,388 A | 10/1989 | Wong et al. | |
| 4,891,225 A | 1/1990 | Langer | |
| 4,906,474 A | 3/1990 | Langer | |
| 4,938,763 A | 7/1990 | Dunn et al. | |
| 4,957,744 A | 9/1990 | Della Valle et al. | |

(Continued)

FOREIGN PATENT DOCUMENTS

| | | |
|---|---|---|
| AU | 8374575 | 8/1975 |
| CA | 2222567 | 12/1996 |

(Continued)

OTHER PUBLICATIONS

U.S. Appl. No. 14/464,624, filed Aug. 20, 2014, Verity.

(Continued)

*Primary Examiner* — Shaojia A Jiang
*Assistant Examiner* — Michael C Henry
(74) *Attorney, Agent, or Firm* — Carol L. Francis; Bozicevic, Field & Francis LLP

(57) ABSTRACT

The present invention is related to methods for lowering peroxide levels in sucrose acetate isobutyrate formulations and to composition used in and formed by such methods.

22 Claims, 6 Drawing Sheets

(56) References Cited

U.S. PATENT DOCUMENTS

| | | |
|---|---|---|
| 4,970,075 A | 11/1990 | Oshlack |
| 4,990,341 A | 2/1991 | Goldie et al. |
| 5,034,229 A | 7/1991 | Magruder et al. |
| 5,057,318 A | 10/1991 | Magruder et al. |
| 5,059,423 A | 10/1991 | Magruder et al. |
| 5,110,596 A | 5/1992 | Magruder et al. |
| 5,112,614 A | 5/1992 | Magruder et al. |
| 5,137,727 A | 8/1992 | Eckenhoff |
| 5,149,543 A | 9/1992 | Cohen |
| 5,151,093 A | 9/1992 | Theeuwes et al. |
| 5,188,837 A | 2/1993 | Domb |
| 5,192,743 A | 3/1993 | Hsu et al. |
| 5,219,572 A | 6/1993 | Sivaramakishnan et al. |
| 5,234,692 A | 8/1993 | Magruder et al. |
| 5,234,693 A | 8/1993 | Magruder et al. |
| 5,266,331 A | 11/1993 | Oshlack et al. |
| 5,278,201 A | 1/1994 | Dunn et al. |
| 5,278,202 A | 1/1994 | Dunn et al. |
| 5,279,608 A | 1/1994 | Cherif Cheikh |
| 5,286,496 A | 2/1994 | Stapler et al. |
| 5,308,348 A | 5/1994 | Balaban et al. |
| 5,312,389 A | 5/1994 | Theeuwes et al. |
| 5,324,519 A | 6/1994 | Dunn et al. |
| 5,324,520 A | 6/1994 | Dunn et al. |
| 5,330,835 A | 7/1994 | Kikuchi et al. |
| 5,336,057 A | 8/1994 | Fukuda et al. |
| 5,340,572 A | 8/1994 | Patel et al. |
| 5,340,849 A | 8/1994 | Dunn et al. |
| 5,350,741 A | 9/1994 | Takada |
| 5,352,662 A | 10/1994 | Brooks et al. |
| 5,356,635 A | 10/1994 | Raman et al. |
| 5,368,588 A | 11/1994 | Bettinger |
| 5,370,864 A | 12/1994 | Peterson et al. |
| 5,382,424 A | 1/1995 | Stapler et al. |
| 5,391,381 A | 2/1995 | Wong et al. |
| 5,399,353 A | 3/1995 | Bartnik et al. |
| 5,399,363 A | 3/1995 | Liversidge et al. |
| 5,442,033 A | 8/1995 | Bezwada |
| 5,456,679 A | 10/1995 | Balaban et al. |
| 5,478,577 A | 12/1995 | Sacklet et al. |
| 5,487,898 A | 1/1996 | Lu et al. |
| 5,505,922 A | 4/1996 | Thut |
| 5,511,355 A | 4/1996 | Dingler |
| 5,540,912 A | 7/1996 | Roorda et al. |
| 5,545,408 A | 8/1996 | Trigg et al. |
| 5,549,912 A | 8/1996 | Oshlack et al. |
| 5,557,318 A | 9/1996 | Gabriel |
| 5,569,450 A | 10/1996 | Duan et al. |
| 5,599,552 A | 2/1997 | Dunn et al. |
| 5,599,852 A | 2/1997 | Scopelianos |
| 5,628,993 A | 5/1997 | Yamagata |
| 5,633,000 A | 5/1997 | Grossman et al. |
| 5,656,295 A | 8/1997 | Oshlack et al. |
| 5,672,360 A | 9/1997 | Sackler et al. |
| 5,702,716 A | 12/1997 | Dunn et al. |
| 5,713,847 A | 2/1998 | Howard, III et al. |
| 5,725,841 A | 3/1998 | Duan et al. |
| 5,728,396 A | 3/1998 | Peery et al. |
| 5,733,950 A | 3/1998 | Dunn et al. |
| 5,736,152 A | 4/1998 | Dunn |
| 5,739,176 A | 4/1998 | Dunn et al. |
| 5,747,051 A | 5/1998 | Granger et al. |
| 5,747,058 A | 5/1998 | Tipton et al. |
| 5,750,100 A | 5/1998 | Yamagata et al. |
| 5,759,563 A | 6/1998 | Yewey et al. |
| 5,777,124 A | 7/1998 | Zavareh et al. |
| 5,780,044 A | 7/1998 | Yewey et al. |
| 5,786,484 A | 7/1998 | Dyer et al. |
| 5,801,012 A | 9/1998 | Soff et al. |
| 5,836,935 A | 11/1998 | Ashton et al. |
| 5,840,329 A | 11/1998 | Bai |
| 5,874,388 A | 2/1999 | Hsu |
| 5,879,705 A | 3/1999 | Heafield et al. |
| 5,919,473 A | 7/1999 | Elkhoury |
| 5,932,597 A | 8/1999 | Brown |
| 5,942,241 A | 8/1999 | Chasin et al. |
| 5,968,542 A | 10/1999 | Tipton |
| 5,976,109 A | 11/1999 | Hemth |
| 5,985,305 A | 11/1999 | Peery et al. |
| 5,994,548 A | 11/1999 | Langston et al. |
| 5,997,527 A | 12/1999 | Gumucio et al. |
| 5,997,902 A | 12/1999 | Maruyama et al. |
| 6,008,355 A | 12/1999 | Huang et al. |
| 6,042,811 A | 3/2000 | Duan et al. |
| 6,051,558 A | 4/2000 | Burns et al. |
| 6,093,420 A | 7/2000 | Baichwal |
| 6,113,938 A | 9/2000 | Chen et al. |
| 6,126,919 A | 10/2000 | Stefely et al. |
| 6,130,200 A | 10/2000 | Brodbeck et al. |
| 6,132,420 A | 10/2000 | Dionne et al. |
| 6,143,322 A | 11/2000 | Sacl<ler et al. |
| 6,156,331 A | 12/2000 | Peery et al. |
| 6,203,813 B1 | 3/2001 | Gooberrnan |
| 6,217,906 B1 | 4/2001 | Gumucio et al. |
| 6,245,351 B1 | 6/2001 | Nara et al. |
| 6,248,112 B1 | 6/2001 | Gambale et al. |
| 6,261,584 B1 | 7/2001 | Peery et al. |
| 6,270,787 B1 | 8/2001 | Ayer |
| 6,283,948 B1 | 9/2001 | Roorda |
| 6,291,013 B1 | 9/2001 | Gibson et al. |
| 6,312,717 B1 | 11/2001 | Molinoff et al. |
| 6,375,978 B1 | 4/2002 | Kleiner et al. |
| 6,384,227 B2 | 5/2002 | Dyer et al. |
| 6,395,292 B2 | 5/2002 | Peery et al. |
| 6,403,609 B1 | 6/2002 | Asgherian |
| 6,413,536 B1 | 7/2002 | Gibson et al. |
| 6,420,454 B1 | 7/2002 | Wenz et al. |
| 6,426,339 B1 | 7/2002 | Berde et al. |
| 6,436,091 B1 | 8/2002 | Harper et al. |
| 6,440,493 B1 | 8/2002 | Gibson et al. |
| 6,447,522 B2 | 9/2002 | Gambale et al. |
| 6,468,961 B1 | 10/2002 | Brodbeck et al. |
| 6,479,074 B2 | 11/2002 | Murdock et al. |
| 6,486,138 B1 | 11/2002 | Asgherian et al. |
| 6,498,153 B1 | 12/2002 | Cady et al. |
| 6,508,808 B1 | 1/2003 | Carr et al. |
| 6,514,516 B1 | 2/2003 | Chasin et al. |
| 6,521,259 B1 | 2/2003 | Chasin et al. |
| 6,524,607 B1 | 2/2003 | Goldenheim et al. |
| 6,525,102 B1 | 2/2003 | Chen et al. |
| 6,699,908 B2 | 3/2004 | Sackler |
| 6,733,783 B2 | 5/2004 | Oshlack |
| 6,840,931 B2 | 1/2005 | Peterson et al. |
| 6,921,541 B2 | 7/2005 | Chasin et al. |
| 6,992,065 B2 | 1/2006 | Okumu |
| 7,053,209 B1 | 5/2006 | Gibson et al. |
| 7,833,543 B2 | 11/2010 | Gibson et al. |
| 8,133,507 B2 | 3/2012 | Yum et al. |
| 8,147,870 B2 | 4/2012 | Yum et al. |
| 8,153,149 B2 | 4/2012 | Verity |
| 8,153,152 B2 | 4/2012 | Yum et al. |
| 8,153,661 B2 | 4/2012 | Verity |
| 8,168,217 B2 | 5/2012 | Yum et al. |
| 8,231,903 B2 | 7/2012 | Fraatz et al. |
| 8,337,883 B2 | 12/2012 | Yum et al. |
| 8,354,124 B2 | 1/2013 | Yum et al. |
| 8,415,401 B2 | 4/2013 | Yum et al. |
| 8,420,120 B2 | 4/2013 | Yum et al. |
| 8,496,943 B2 | 7/2013 | Fereira et al. |
| 8,753,665 B2 | 6/2014 | Verity |
| 8,846,072 B2 | 9/2014 | Verity |
| 8,945,614 B2 | 2/2015 | Yum et al. |
| 8,951,556 B2 | 2/2015 | Yum et al. |
| 2001/0000522 A1 | 4/2001 | Dyer et al. |
| 2001/0029257 A1 | 10/2001 | Murdock et al. |
| 2002/0001631 A1 | 1/2002 | Okumu |
| 2002/0064536 A1 | 5/2002 | Hunt |
| 2002/0114835 A1 | 8/2002 | Sackler et al. |
| 2002/0173552 A1 | 11/2002 | Cleland et al. |
| 2003/0044467 A1 | 3/2003 | Brodbeck et al. |
| 2003/0045454 A1 | 3/2003 | Okumu et al. |
| 2003/0059376 A1 | 3/2003 | Libbey et al. |
| 2003/0108609 A1 | 6/2003 | Berry et al. |
| 2003/0114430 A1 | 6/2003 | MacLeod et al. |

(56) References Cited

U.S. PATENT DOCUMENTS

| | | |
|---|---|---|
| 2003/0152637 A1 | 8/2003 | Chasin et al. |
| 2003/0170289 A1 | 9/2003 | Chen et al. |
| 2003/0180364 A1 | 9/2003 | Chen et al. |
| 2003/0185873 A1 | 10/2003 | Chasin et al. |
| 2003/0215515 A1 | 11/2003 | Truong-le et al. |
| 2004/0001889 A1 | 1/2004 | Chen et al. |
| 2004/0024021 A1 | 2/2004 | Sudo et al. |
| 2004/0024069 A1 | 2/2004 | Chen et al. |
| 2004/0042194 A1 | 3/2004 | Hsieh |
| 2004/0052336 A1 | 3/2004 | Langlet et al. |
| 2004/0101557 A1 | 5/2004 | Gibson et al. |
| 2004/0109893 A1 | 6/2004 | Chen et al. |
| 2004/0138237 A1 | 7/2004 | Shah |
| 2004/0142902 A1 | 7/2004 | Struijker-Boudier |
| 2004/0146562 A1 | 7/2004 | Shah |
| 2004/0151753 A1 | 8/2004 | Chen et al. |
| 2004/0161382 A1 | 8/2004 | Yum et al. |
| 2004/0208845 A1 | 10/2004 | Michal et al. |
| 2004/0224019 A1 | 11/2004 | Zale et al. |
| 2004/0224903 A1 | 11/2004 | Berry et al. |
| 2005/0008661 A1 | 1/2005 | Fereira et al. |
| 2005/0042194 A1 | 2/2005 | Ng et al. |
| 2005/0095284 A1 | 5/2005 | Trautman |
| 2005/0106214 A1 | 5/2005 | Chen |
| 2005/0106304 A1 | 5/2005 | Cook et al. |
| 2005/0171052 A1 | 8/2005 | Cook et al. |
| 2005/0232876 A1 | 10/2005 | Minga et al. |
| 2005/0244489 A1 | 11/2005 | Paris |
| 2005/0266087 A1 | 12/2005 | Junnarkar et al. |
| 2005/0276856 A1 | 12/2005 | Fereira et al. |
| 2005/0281879 A1 | 12/2005 | Chen et al. |
| 2006/0034926 A1 | 2/2006 | Fraatz et al. |
| 2006/0058401 A1 | 3/2006 | Ishikawa et al. |
| 2006/0165800 A1 | 7/2006 | Chen et al. |
| 2006/0210599 A1 | 9/2006 | Gibson et al. |
| 2008/0023261 A1 | 1/2008 | Kaneko et al. |
| 2008/0145419 A1 | 6/2008 | Gibson et al. |
| 2008/0152708 A1 | 6/2008 | Gibson et al. |
| 2008/0167630 A1 | 7/2008 | Verity |
| 2008/0206321 A1 | 8/2008 | Yum et al. |
| 2008/0287464 A1 | 11/2008 | Wright et al. |
| 2009/0023689 A1 | 1/2009 | Yum et al. |
| 2009/0023690 A1 | 1/2009 | Yum et al. |
| 2009/0036490 A1 | 2/2009 | Verity |
| 2009/0037490 A1 | 2/2009 | Ohira |
| 2009/0215808 A1 | 8/2009 | Yum et al. |
| 2009/0298862 A1 | 12/2009 | Yum et al. |
| 2011/0009451 A1 | 1/2011 | Verity |
| 2012/0135072 A1 | 5/2012 | Yum et al. |
| 2012/0135073 A1 | 5/2012 | Yum et al. |
| 2012/0177697 A1 | 7/2012 | Chen |
| 2013/0251674 A1 | 9/2013 | Fereira et al. |
| 2013/0281480 A1 | 10/2013 | Yum et al. |
| 2013/0287845 A1 | 10/2013 | Yum et al. |
| 2013/0289053 A1 | 10/2013 | Wright et al. |
| 2013/0289069 A1 | 10/2013 | Verity |
| 2013/0295168 A1 | 11/2013 | Yum et al. |
| 2013/0317049 A1 | 11/2013 | Yum et al. |
| 2013/0337059 A1 | 12/2013 | Yum et al. |
| 2013/0337060 A1 | 12/2013 | Yum et al. |
| 2013/0345260 A1 | 12/2013 | Gibson et al. |
| 2014/0275147 A1 | 9/2014 | Yum et al. |
| 2014/0308352 A1 | 10/2014 | Wright et al. |
| 2015/0196644 A1 | 7/2015 | Yum et al. |

FOREIGN PATENT DOCUMENTS

| | | |
|---|---|---|
| CA | 2283517 | 4/1998 |
| CA | 2291087 | 12/1998 |
| CA | 2303442 | 3/1999 |
| DE | 1569231 A1 | 8/1969 |
| DE | 2213717 A1 | 11/1972 |
| DE | 2321174 A1 | 11/1973 |
| DE | 2438352 A1 | 2/1976 |
| DE | 2720245 A1 | 11/1977 |
| DE | 19520237 | 12/1996 |
| DE | 19714765 A1 | 10/1998 |
| EP | 0244118 | 11/1987 |
| EP | 0290983 | 11/1988 |
| EP | 0413528 | 2/1991 |
| EP | 0539751 | 10/1991 |
| EP | 0535899 | 4/1993 |
| EP | 0537559 | 4/1993 |
| EP | 0539559 | 5/1993 |
| EP | 0621042 | 10/1994 |
| EP | 0635531 | 1/1995 |
| EP | 0640336 | 3/1995 |
| EP | 0671162 | 9/1995 |
| EP | 0711548 | 5/1996 |
| EP | 0773034 | 5/1997 |
| EP | 0999825 | 5/2000 |
| EP | 1010436 | 6/2000 |
| EP | 0782569 | 3/2002 |
| EP | 0804417 | 6/2003 |
| EP | 0788480 | 7/2003 |
| EP | 0788481 | 8/2003 |
| EP | 1348427 | 10/2003 |
| EP | 1032390 | 11/2003 |
| EP | 0778768 | 5/2004 |
| EP | 15480093 | 6/2005 |
| EP | 1212092 | 10/2005 |
| EP | 2238478 | 10/2010 |
| GB | 1088992 A | 10/1967 |
| GB | 2238478 | 6/1991 |
| JP | S59210024 A | 11/1984 |
| JP | S62000419 A | 1/1987 |
| JP | 63302858 | 12/1988 |
| JP | 2096516 A | 4/1990 |
| JP | H05194273 A | 8/1993 |
| JP | H0753356 A | 2/1995 |
| JP | 07070297 | 3/1995 |
| JP | H07112940 A | 5/1995 |
| JP | H07115901 A | 5/1995 |
| JP | H07124196 A | 5/1995 |
| JP | 8505395 | 6/1996 |
| JP | 08206191 | 8/1996 |
| JP | 8512303 | 12/1996 |
| JP | H09502181 A | 3/1997 |
| JP | 2000185091 | 7/2000 |
| JP | 4330175 | 6/2009 |
| JP | 4501076 | 7/2010 |
| WO | WO1990003768 | 4/1990 |
| WO | WO1990003809 | 4/1990 |
| WO | WO1991016929 | 11/1991 |
| WO | WO1991017900 | 11/1991 |
| WO | WO1991018016 | 11/1991 |
| WO | WO1992017900 | 10/1992 |
| WO | WO1993000006 | 1/1993 |
| WO | WO1993003751 | 3/1993 |
| WO | WO1993007833 | 4/1993 |
| WO | WO1994005265 | 3/1994 |
| WO | WO1994015587 | 7/1994 |
| WO | WO1995001786 | 1/1995 |
| WO | WO1995006693 | 3/1995 |
| WO | WO1995009613 | 4/1995 |
| WO | WO1995017901 | 7/1995 |
| WO | WO1996009290 | 3/1996 |
| WO | WO1996012699 | 5/1996 |
| WO | WO1996012700 | 5/1996 |
| WO | WO1996022281 | 7/1996 |
| WO | WO1996039995 | 12/1996 |
| WO | WO1996041616 | 12/1996 |
| WO | WO1997015285 | 5/1997 |
| WO | WO1997027840 | 8/1997 |
| WO | WO1997049391 | 12/1997 |
| WO | WO1998027962 | 7/1998 |
| WO | WO1998027963 | 7/1998 |
| WO | WO1998034596 | 8/1998 |
| WO | WO1998044903 | 10/1998 |
| WO | WO1998051246 | 11/1998 |
| WO | WO1998053837 | 12/1998 |
| WO | WO1999006023 | 2/1999 |
| WO | WO1999013913 | 3/1999 |
| WO | WO1999025349 | 5/1999 |

(56) References Cited

FOREIGN PATENT DOCUMENTS

| WO | WO1999033446 | 7/1999 |
|---|---|---|
| WO | WO2000000120 | 1/2000 |
| WO | WO2000000181 | 1/2000 |
| WO | WO2000033866 | 6/2000 |
| WO | WO2000045790 | 8/2000 |
| WO | WO2000054745 | 9/2000 |
| WO | WO2001 043528 | 12/2000 |
| WO | WO2000078335 | 12/2000 |
| WO | WO2001042518 | 12/2000 |
| WO | WO2001015734 | 3/2001 |
| WO | WO2001051024 | 7/2001 |
| WO | WO2001051041 | 7/2001 |
| WO | WO2001 076599 | 10/2001 |
| WO | WO2001 078983 | 10/2001 |
| WO | WO2001 049336 | 12/2001 |
| WO | WO200201 0436 | 2/2002 |
| WO | WO2002028366 | 4/2002 |
| WO | WO2002043800 | 6/2002 |
| WO | WO2002053187 | 7/2002 |
| WO | WO2002067895 | 9/2002 |
| WO | WO2003000282 | 1/2003 |
| WO | WO2003041684 | 5/2003 |
| WO | WO2003041757 | 5/2003 |
| WO | WO2003072113 | 9/2003 |
| WO | WO2003086368 | 10/2003 |
| WO | WO2003101358 | 12/2003 |
| WO | WO2003101961 | 12/2003 |
| WO | WO2004007451 | 1/2004 |
| WO | WO2004011032 | 2/2004 |
| WO | WO2004037224 | 5/2004 |
| WO | WO2004037289 | 5/2004 |
| WO | WO2004052336 | 6/2004 |
| WO | WO2004056338 | 7/2004 |
| WO | WO2004082658 | 9/2004 |
| WO | WO2004089335 | 10/2004 |
| WO | WO2004101557 | 11/2004 |
| WO | WO2005009408 | 2/2005 |
| WO | WO20050487 44 | 6/2005 |
| WO | WO2005048930 | 6/2005 |
| WO | WO2005049069 | 6/2005 |
| WO | WO2005105031 | 11/2005 |
| WO | WO2005115333 | 12/2005 |
| WO | WO2006033948 | 3/2006 |
| WO | WO2006083950 | 8/2006 |
| WO | WO2006084139 | 8/2006 |
| WO | WO2006084140 | 8/2006 |
| WO | WO2006084141 | 8/2006 |
| WO | WO2008023261 | 2/2008 |
| WO | WO2014144984 | 9/2014 |

OTHER PUBLICATIONS

"3M DDS Announces Development of New HFA-Compatible Excipients: Novel Oligomeric Acids as MDI Suspension Aids and Solubilizers," (2000) *3M Delivery*.

Adams EG, et al. "A comparison of the abuse liability oftramadol, NSAIDS, and hydrocodone in patients with chronic pain." Journal of Pain and Symptom Management. 31(5), 465-4 76 2006.

Ahuja et al. (1995) "Intra-Articular Morphine Versus Bupivacaine for Postoperative Analgesia Following Knee Arthroscopy" *The Knee* 2(4):227-231.

Ajayaghosh, A., et al., "Solid-Phase Synthesis of N-Methyl and N-Ethylamides of Peptides Using Photolytically Detachable ((3-Nitro-4-((alkylamino)methyl)benzamido)methyl)polystrene Resin," J. Org. Chem., 55:2826 (1990).

Allahham A, et al. "Flow and injection characteristics of pharmaceutical parenteral formulations using a micro-capillary rheometer". Int J Pharm. 2004;270(1-2): 139-48.

Ansel, H.C. et al., Pharmaceutical Dosage Forms and Drug Delivery System, sixth ed., (1995).

Barb, R. et al., "Evaluation of the Saber Delivery System for the Controlled Release of Deslorelin: Effect of Dose in Estrogen Primed Ovarectomized Gilts," Proceed. lnt'I Symp. Control. Rel. Bioact. Mater. 26 (1999).

Bartfield et al. (1998) "Randomized Trial of Diphenhydramine Versus Benzyl Alcohol with Epinephrine as an Alternative to Lidocaine Local Anesthesia" *Ann Emerg Med* 32(6):650-654.

Bartfield et al. (2001) "Benzyl Alcohol with Epinephrine as an Alternative to Lidocaine With Epinephrine" *J Emerg Med* 21(4):375-379.

Bartosz, et al., (1997) "Antioxidant and Prooxidant Properties of Captopril and Enalapril",Free Radical Biology & Medicine, 23(5):729-735.

Becker, S.E., et al. "Effects of Gonadotropin-Releasing Hormone Infused in a Pulsatile or Continuous Fashion on Serum Gonadotropin Concentrations and Ovulation in the Mare," J. Anim. Sci. (1992) 70:1208-1215.

Bekersky I, et al. "Effect oflow- and high-fat meals on tacrolimus absorption following 5 mg single oral doses to healthy human subjects." J Clin Pharmacol 2001; 41(2): 176-82.

Betschart, R., et al., "Evaluation of the Saber.TM. Delivery System for the Controlled Release of the GnRH Analogue Deslorelin for Advancing Ovulation in Mares: Effect of Gamma Radiation"; Proceed. lnt'I Symp. Control. Rel. Bioact. Mater. 25 (1998) Controlled Release Society, Inc. pp. 655-656.

Bhatia & Singh "Percutaneous Absorption of LHRH Through Porcine Skin: Effect of N-Methyl 2-Pyrrolidone and Isopropyl Myristate"; *Drug Development & Industrial Pharmacy* 23(11):1113-1114 (1997).

Brevard J, et al. "Pain and opioid abuse in a population of substance abuse patients: data from the NA VIPPRO system"; Conference paper presented at the 42nd American Pain Society (APS) Annual Scientific Meeting, Washington, D.C. 2007.

Buhler, K., GnRH Agonists and Safety, in GnRH Analagoues the State of the Art 1993, a Summary of the 3rd International Symposium on GnRH Analogues in Cancer and Human Reproduction, Geneva, Feb. 1993.

Burns, P. et al., "Pharmacodynamic Evaluation of the Saber.TM. Delivery System for the Controlled Release of the GnRH Analogue Deslorelin Acetate for Advancing-Ovulation in Cyclic Mares," Proceed. lnt'I. Symp. Control. Rel. Bioact. Mater., 24 (1997), Controlled Release Society, Inc.

Cellulose Acetate Butyrate. In: European pharmacopoeia. 4 edn. Strasbourg Cedex, France: Council of Europe; 2001; p. 853-4.

Coy, et al., "Solid Phase Synthesis of Lutcinizing Hormone-Releasing Hormone and Its Analogs," Methods Enzymol. 37, 416 (1975).

D 2857-95 (2001) "Standard Practice for Dilute Solution Viscosity of Polymers" Copyright by ASTM lnt'l.

DE, Asim K. and DE, Avik, (2014), "Reaction Rate Constants for Hydrogen Peroxide Oxidation of Phenol and Chlorinated Phenols in a Continuous Stirred Tank Reactor", International Journal of Engineering Research & Technology (IJERT), 3(6):222-226.

Desai et al., "Surface Modification of Polymeric Biomaterials for Reduced Thrombogenicity," Polym. Mater. Sci. Eng., 62:731-735 (1990).

Dodson, K.M., et al. "Oral Controlled Release of Antiretrovirals Using the SABER Delivery System Incorporated into Soft Gelatin Capsules", AAPS Meeting, 1999, New Orleans, LA.

Duan, D. et al., "Novel Dispersing Aids for Hydrofluoroalkane-Based Metered Dose Inhalers," 1998 Conference of the American Association of Pharmaceutical Scientists, San Francisco, California, Nov. 1998.

Duan, D. et al., "Oligomeric Lactic Acids as Solubilizing Aids for HFA-Based Metered Dose Inhalers," 1998 Conference of the American Association of Pharmaceutical Scientists, San Francisco, California, Nov. 1998.

Dunbar SA, Katz NP "Chronic opioid therapy for nonmalignant pain in patients with a history of substance abuse: report of20 cases." Journal of Pain and Symptom Management. 11 (3), 163-1 7 1. 1996.

English Translation of Japanese Office Action dated Mar. 6, 2012 for Japanese Patent Application No. 2009-108881.

English Translation of Japanese Office Action dated Mar. 6, 2012 for Japanese Patent Application No. 2009-2735.

(56) References Cited

OTHER PUBLICATIONS

Fitzgerald, B.P, et al., "Effect of Constant Administration of a Gonadotropin-Releasing Hormone Agonist on Reproductive Activity in Mares: Preliminary Evidence on Suppression of Ovulation During the Breeding Season," Am. J. Vet. Res., 1993, 54(10):1746-1751.
Fleury, J., et al., "Evaluation of the Saber.TM. Delivery System for the Controlled Release of the Deslorelin for Advancing Ovulation in the Mare: Effects of Formulation & Dose," Proceed. Int'I. Symp. Control. Rel. Bioact. Mater. 25 (1998) Controlled Release Society, Inc. pp. 657-658.
Gilderman L., et al. "RemoxyJM: a New Opioid Drug with Effective Analgesia and Abuse-Resistance." American Pain Society Annual Meeting, San Antonio, TX, May 2006.
Ginther, O.J., Reproductive Biology of the Mare: Basic and Applied Aspects, EquiServices, Chapter 12, 499-508 Cross Plains, Wisconsin (1970).
Ginther, O.J. et al. "Effect of a Synthetic Gonadotropin-Releasing Hormone on Plasma Concentrations of Luteinizing Hormone in Ponies," Am. J. Vet. Res., 35: 79-81 (1974).
Ginther, O.J., "Ultrasonic Imaging and Reproductive Events in the Mare," Equiservices, Cross Plains, WI Chapter 4:43-72 (1986).
Glajchen, M. "Chronic Pain: Treatment Barriers and Strategies for Clinical Practice." JAM Board Fam Pract. 2001, 14(3): 178-183.
Harrison, L., et al. "Comparison of HCG, Buserelin and Luprostiol for Induction of Ovulation in Cycling Mares," J. Eq. Vet. Sci., 11:163-166 (1991).
Hatakeyama et al., "Synthesis and physical properties of polyurethanes from saccharide-based polycaprolactones." Macromolecular Symposia, vol. 130, pp. 127-138, 1998.
Hays LR. "A profile of OxyContin addiction"; Journal of Addictive Diseases 23(4), 1-9. 2004.
Henry (1995) "Sucrose Acetate Isobutyrate Special Grade for Beverage Applications" International Food Ingredients No. 1 p. 47.
Hoskin PJ, et al. "The bioavailability and pharmacokinetics of morphine after intravenous, oral and buccal administration in healthy volunteers." Br J Clin Pharmacol 1989; 27 (4):499-505.
Hoffmann, M.R. and Edwards, J.O., (1975) "Kinetics of the Oxidation of Sulfite by Hydrogen Peroxide in Acidic Solution", The Journal of Physical Chemistry, 79(20):2096-2098.
Hyland, J.H., et al. "Infusion of Gonadotrophin-Releasing Hormone (GnRH) Induces of Ovulation and Fertile Oestrus in Mares During Seasonal Anoestrus," J. Reprod. Fert., Suppl. 35 (1987):211-220.
Inciardi et al. (2007) "Mechanisms of prescription drug diversion among drug-involved club and street-based populations" Pain Medicine. 8(2), 17 1-183.
Irvine, C.H.G., "GnRH Clinical Application,"; In Equine Reproduction, (eds) McKinon, A.O. and Voss, J.L., Chapter 36, pp. 41-45, Lea & Febiger (1993).
Irvine, D.S., "Duration of Oestrus and Time of Ovulation in Mares Treated with Synthetic GnRH (Ay24,031)," J. Reprod. Fert. Supp. 23:279-283 (1975).
Ishida T, Oguri K, et al. "Isolation and identitication of urinary metabolites of oxycodone in rabbits." Drug Metab Dispos 1979; 7 (3): 162-5.
Ishida T, Oguri K, Yoshimura H. "Determination of oxycodone metabolites in urines and feces of several mammalian species." J Pharmacobiodyn 1982; 5 (7):52 1-5.
Iyakuhin (1974) "Jitsuyo lyakuhin Tenkabutsu (Practical Medical Additives)" Kagaku Kogyo-sha, Tokyo.
Japanese Office Action for Japanese Patent Application No. 2007-532447 dated Nov. 15, 2011.
Jochle, W., et al., Control of Ovulation in the Mare with Ovuplant. TM., a Short-Term Release Implant (STI) Containing the GNRH Analogue Deslorelin Acetate: J. Eq. Vet. Sci., 44:632 (1994).
Johnson & Verity (2002) "Applications of Continuous Site-Directed Drug Delivery" *Proc West Pharmacal Soc* 45:219-222.
Johnston LO, O'Malley PM, Bachman JG, Schulenberg, JE. "Monitoring the future. National results on adolescent drug use: overview of key findings" (NIH Publication No. 05-5726). Bethesda MD: National Institute on Drug Abuse 2004.
Kasraian et al. (1999) "Developing an Injectable Formula Containing an Oxygen-Sensitive. Drug: a Case Study of Danofloxacin Injectable" Pharm Dev Technol 4(4):475-480.
Katz NP, et al. "Behavioral monitoring and urine toxicology testing in patients receiving longterm opioid therapy." Anesth Analg. 97(4), 1097-1102, (2003).
Katz NP, et al. "Challenges in the development of prescription opioid abuse-deterrent formulations." Clin J Pain. 2007;23(8):648-60.
Katz NP, et al. "Development and preliminary experience with an ease of extractability rating system for prescription opioids." Drug Development and Industrial Pharmacy. 32(6) 727-746(20). 2006.
Katz NP, et al. "Prescription monitoring of medical and non-medical Schedule $u$ opioid abuse in Massachusetts: 1996-2005." Conference paper presented at the 69th College on Problems of Drug Dependence (CPDD). Quebec Canada 2007.
Kim et al. (2001) "Comparing the Effect on Protein Stability of Methionine Oxidation Versus Mutagenesis: Steps Toward Engineering Oxidative Resistance in Proteins" Protein Engineerinq 14(5):343-347.
Kulkarni et al., "Polyactic Acid for Surgical Implants,"; Arch. Surg., 93:389 (1966).
Lacoste, D., et al., "Reversible inhibition of testicular androgen secretion by 3-, 5- and 6-month controlled-release microsphere formulations of the LH-RH agonist [d-Trp6, des-Gly-NH210] LH-RH ethylamide in the dog"; J. Steroid Biochem. 33:5, 1007-1011 (1989).
Lalovic B, et al. "Pharmacokinetics and pharmacodynamics of oral oxycodone in healthy human subjects: role of circulating active metabolites" Clin Pharmacol Ther 2006; 79(5):461-79.
Lapenna, Domenico, et al., (1995) "The Prooxidant Properties of Captopril", Biochemical Pharmacology, 50(1):27-32.
Li, Shihong, et al., (1993) "Chemical Pathways of Peptide Degradation. V. Ascorbic Acid Promotes Rather than Inhibits the Oxidation of Methionine to Methionine Sulf oxide in Small Model Peptides", Pharmaceutical Research, 10(11):1572-1579.
Loy, R.G. et al. "The Effects of Human Chorionic Gonadotrophin on Ovulation, Length of Estrus, and Fertility in the Mare," Cornell Vet. 56:41-50 (1966).
Lu, Jian-Ming, et al., (2010) "Chemical and molecular mechanisms of antioxidants: experimental approaches and model systems", J. Cell. Mol. Med., 14(4):840-860.
Material Safety Data Sheet of Eastman Chemical Products, "SAIB" Sucrose Acetate Isobutyrate, pp. 2-18.
Material Safety Data Sheet of Eastman Chemical Products, "SAIB" Sucrose Acetate lsobutyrate, Publication GN-311 F (Jun. 2004).
Material Safety Data Sheet of Eastman Fine Chemicals, "Sucrose Acetate Isobutyrate, Special Grade (SAIB-SG)," Publication No. EFC-211, May 1991.
Material Safety Data Sheet of Eastman Products for the Food Industry, "Sucrose Acetate lsbutyrate (SAIB-SB) for Use in Fruit-Flavored Beverages," Publication No. ZM-90, pp. 2-7 (Sep. 1989).
McCabe et al. "Motives, diversion and routes of administration associated with nonmedical use of prescription opioids." Addictive Behaviors. 32, 562-575. 2007.
McLellan AT, Luborsky L, Woody GE, O'Brien CP. "An improved diagnostic instrument for substance abuse patients." The Addiction Severity Index. J Nerv Ment Dis. 1980; 168:26-33.
Mearns, "Changing Seasons," The Blood-Horse, Sep. 28, 1996, 4794-4795.
McCarthy, P. et al., "Management of Stallions on Large Breeding Farms," Stallion Management, vol. 8, No. 1, Apr. 1992, pp. 219-235.
McKinnon, A.O., et al. "Effect of a GnRH Analogue (Ovuplant), hCG and Dexamethasone on Time to Ovulation in Cycling Mares." World Equine Veterinary Review, (1997) 2:3 16-18.
McKinnon, A.O., et al. "Repeated Use of a GnRH Analogue Deslorelin (Ovuplant) for Hastening Ovulation in the Transitional Mare," Equine Vet. J., (1996) 29:2 153-155.
Merrifield, B., "Solid phase synthesis"; Science 232:342 (1986).

(56) References Cited

OTHER PUBLICATIONS

Meyer RJ, et al. Awareness topic: mitigating the risk of ethanol induced dose dumping from oral sustained controlled release dosage forms. In: FDA's Advisory Committee for Pharmaceutical Science Meeting, Oct. 2005.

Montovan, S.M., et al., "The Effect of a Potent GnRH Agonist on Gonadal and Sexual Activity in the Horse," Theriogenology, 33:6, 1305-1321 (1990).

Mumford, E.L. et al., "Use of Deslorelin Short-Term Implants to Induce Ovulation in Cycling Mares During Three Consecutive Estrov Cycles," Animal Reproduction Science, 139 (1995) 129-140.

Murray S, et al. "Alcohol-associated rapid release of a long-acting opioid" CMAJ 2005; 173(7):756.

Nakagaki (1968) "Seizai Butsuri Kagaku (Physical Chemistry of Medical Preparations)," Asakura Shoten, Tokyo.

Nally, J., et al., "Induction of Mucosal lgA Specific for SeMF3 for *Streptococcus equi* with Intranasal Vaccination Using a Sucrose Acetate lsobutyrate Based Delivery System", Proceed. lnt'l. Symp. Control. Rel. Bioact. Mater. 26 (1999) Controlled Release Society, Inc.

Nett et al., "Further Studies on the Radioimmunoassay of Gonadotropin-Releasing Hormone: Effect of Radioiodination, Antiserum and Unextracted Serum on Levels of lmmunoreactivity in Serum," Endocrinology 101:1135 (1977).

"New Drugs/Programs", Current Drug Discovery, Nov. 2004 pp. 7-10.

"Polycaprolactone" https://en.wikipedia.org/wiki/Polycaprolactone 1 page, Jun. 16, 2008.

"Polyglycolide" https://en.wikipedia.org/wiki/Polyglycolide 3 pages, printed Jun. 16, 2008.

"Polylactic Acid"; https://en.wikipedia.org/wiki/Polylactic_acid, 1 page, printed Jun. 16, 2008.

Pulido et al., "Enzymatic Regioselective Acylation of Hexoses and Pentoses Using Oxime Esters.", J. Chem. Soc. Perkin Trans. 1, (21), 2891-2898, 1992.

Rabb et al., "Effects of Active lmmunication Against GnRH on LH, FSH and Prolactin Storage, Sectretion and Response to Their Secretagogues in Pony Geldings," J. Anim. Sci., 68:3322-3329 (1990).

Reynolds, R.C. et al., "Sucrose acetate isobutyrate (SAIB): historical aspects of its use in beverages and a review of toxicity studies prior to 1988," Food Chem. Toxicol., 1998,36 (2), pp. 81-93.

Reynolds, R.C., "Metabolism and pharmacokinetics of sucrose acetate isobutyrate (SAIB) and sucrose octaisobutyrate (SOIB) in rats, dogs, monkeys or humans. a review," Food Chem. Toxicol. 1998 36 (2). 95-99.

Roser, J.J., et al., "The Development of Antibodies to Human Chorionic Gonadotrpins Following its Repeated Injection in the Cyclic Mare," J. Reprod. Fert. Suppl., 173-179 (1979).

Sullivan, J., "Duration of Estrus and Ovulation Time in Nonlactating Mares Given Human Chorionic Gonadotropin During Three Successive Estrous Periods," J. Am. Vet. Med. Assoc., 63:895 (1973).

Sullivan, S. A., 1998, "Sustained Release of Orally Administered Active Using SABER™ Delivery System Incorporated into Soft Gelatin Capsules" Proceed. lnt'l Symp. Control. Rel. Bioact. Mater., 25:918-919.

Swiderski et al., "Application of 14C Isotope in Studies of Liability of Sugar Substitutents", Nukleonike, Supl., (1996), 10, 347-52.

Thompson, Jr., D.L., et al., "Effects of Melatonin and Thyrotropin Releasing Hormone of Mares Durign the Nonbreeding Season," J. Anim Sci., 58:3, 668-677(1983).

Thompson, Jr., D.L., et al., "Testosterone Effects on Mares During Synchoronization with Altrenogest: FSH, LH, Estrous, Duration and Pregnancy Rate," J. Anim Sci., 56:3, 678-686 (1983).

Trescot AM, et al. "Opioid Guidelines in the Management of Chronic Non-Cancer Pain." Pain Physician. 2006;9: 1-40.

Troen et al. (2003) "The Atherogenic Effect of Excess Methionine Intake" PNAS 100(5):15089-15094.

University of Utah, Department of Chemical Engineering (2006) "A Viscosity: Viscosity Definitions" http://www.che.utah.edu/department_equipment/Projects_lab/A_Viscometers/ViscosityD efinitions.pdf.

Vega-Rios A, Villalobos H, Mata-Segreda JF. "Acid-catalyzed hydrolysis oftriacylglycerols obeys monoexponential kinetics." Int J Chem Kinet. 1992; 24:887-94.

Voss, J.L. et al. "The Effect of HCG on Duration of Oestrus, Ovulation Time and Fertility in Mares," J. Reprod. Fert., Suppl. 23 (1975) 297-301.

Wilson et al. (1999) "Benzyl Alcohol as an Alternative Local Anesthetic" *Ann Emerg Med* 33(5):495-499.

Lapenna et al., (1995) "The Prooxidant Properties of Captopril," Biochemical Pharmacology, 50(1):27-32.

Li et al., (1993) "Chemical Pathways of Peptide Degradation. V. Ascorbic Acid Promotes Rather than Inhibits the Oxidation of Methionine to Methionine Sulfoxide in Small Model Peptides," Pharmaceutical Research, 10(11)1572-1579.

Sakagami and Satoh, (1997) "Prooxidant action of two antioxidants: ascorbic acid and gallic acid", Anticancer Res., 17:221-224.

Tafazoli et al., (2005) "Prooxidant and Antioxidant Activity of Vitamin E Analogues and Troglitazone," Chem. Res. Toxicol., 18:1567-1574.

Baker, M., et al., "Sulfite supported lipid peroxidation in propofol emulsions," *Anesthesiology* 2002; 97: 1162-7.

Brannan, Robert G., "Reactive sulfur species act as prooxidants in liposomal and skeletal muscle model systems," *J. Agric. Food Chem.*, 2010, 58, 3767-3771.

Cornelli, U., et al., "Bioavailability and antioxidant activity of some food supplements in men and women using the D-Roms test as a marker of oxidative stress," *J. Nutr.*, 131, 3208-3211, 2011.

Elmas, O., et al., "The prooxidant effect of sodium metabisulfite in rat liver and kidney," *Reg. Tox. Pharm.*, 42: 77-82, 2005.

Laggner, H., et al., "Sulfite facilitates LDL lipid oxidation by transition metal ions: a pro-oxidant in wine?" *FEBS Letters*, 579 (2005) 6486-6492.

\* cited by examiner

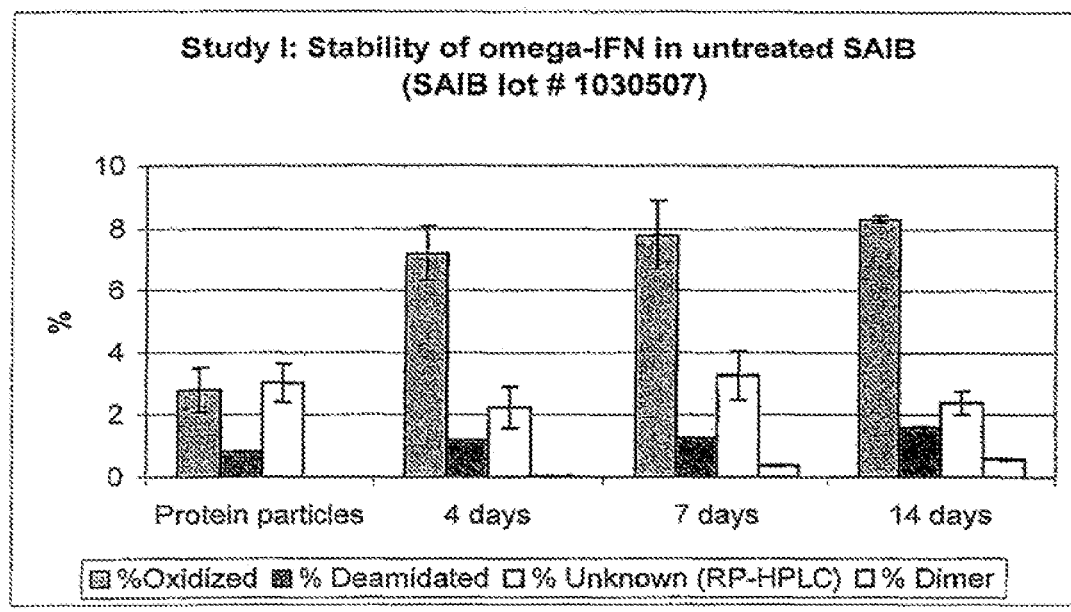
Figure 1. Stability of omega-interferon in untreated SAIB — Study I (n=3)

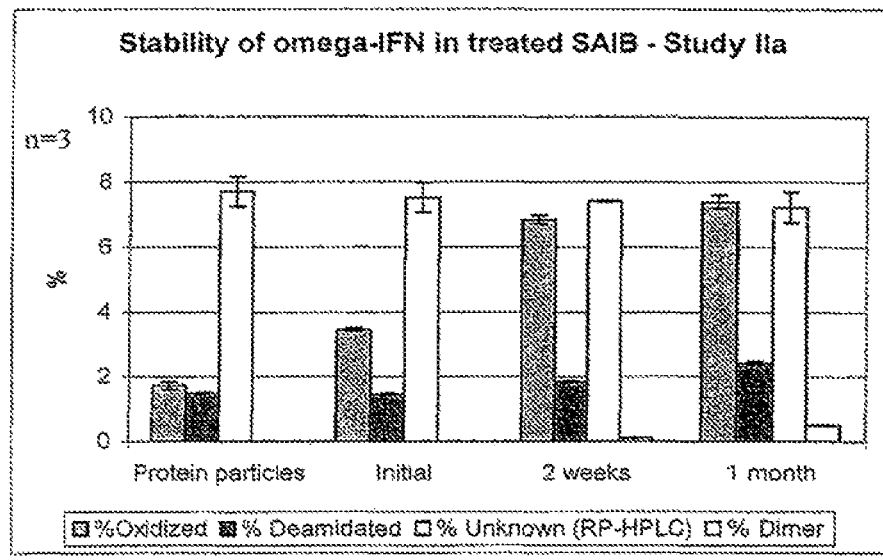
Figure 2. Stability of omega-interferon in alumina treated SAIB        Study IIa
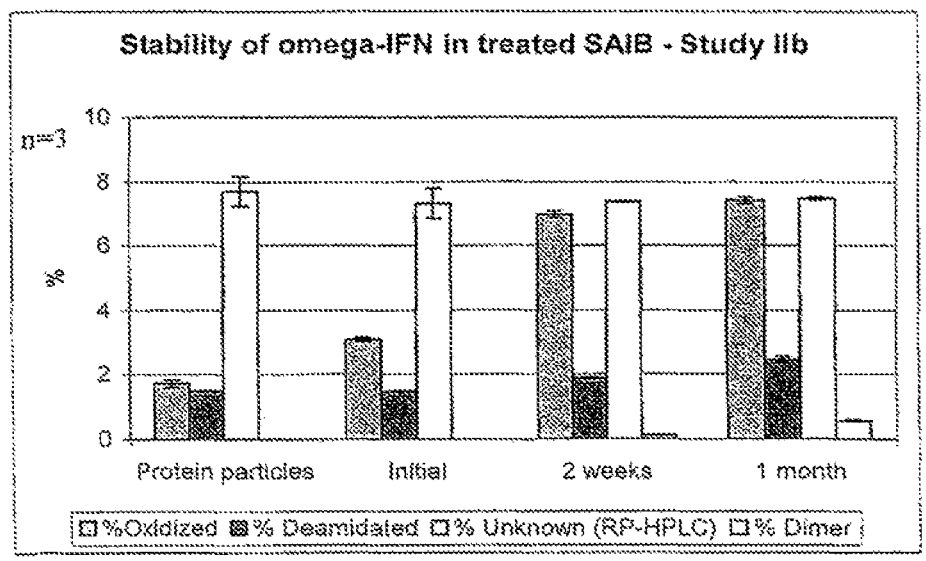
Figure 3. Stability of omega-interferon in alumina treated SAIB        Study IIb

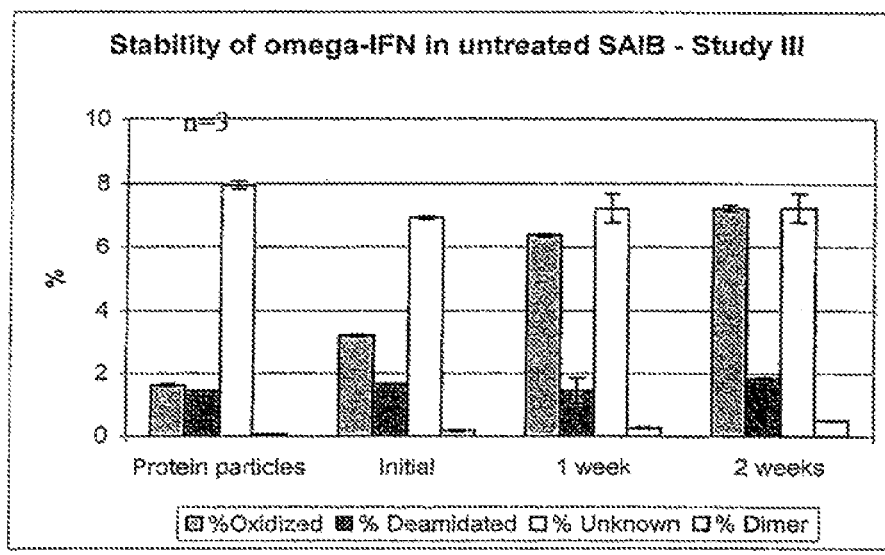
Figure 4. Stability of omega-interferon in untreated SAIB  Study III

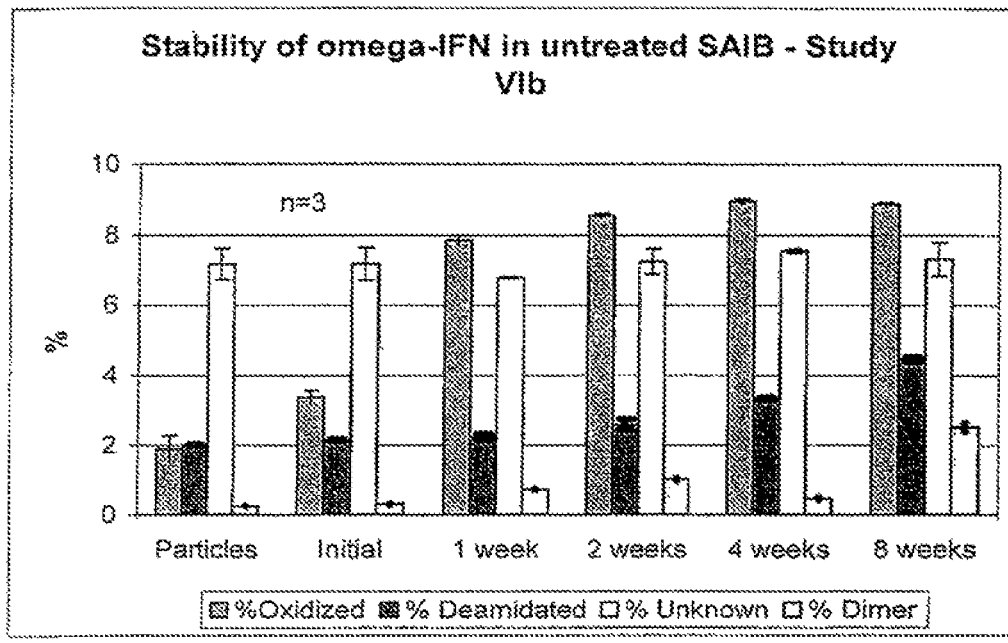
Figure 5. Stability of omega-interferon in untreated SAIB    Study VIb
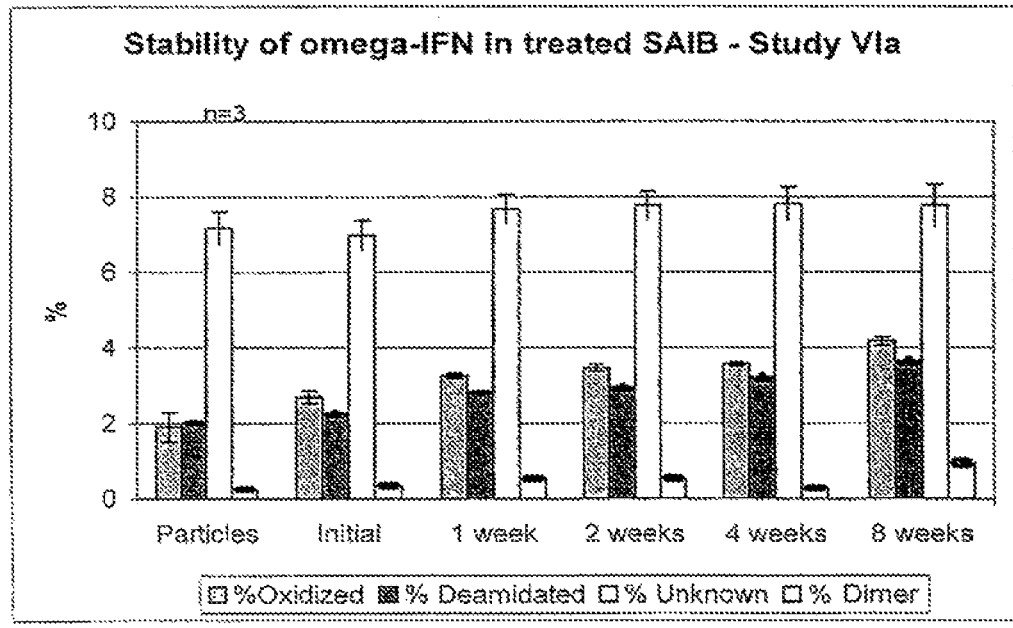
Figure 6. Stability of omega-interferon in sodium metabisulfite treated SAIB
Study VIa Figure 7. Comparison of oxidation of omega-IFN in sodium metabisulfite treated and untreated SAIB

PEROXIDE REMOVAL FROM DRUG DELIVERY VEHICLE

CROSS REFERENCE TO RELATED APPLICATIONS

This application claims the benefit of U.S. provisional application No. 60/702,546, filed Jul. 26, 2005, which is incorporated herein in its entirety.

FIELD OF THE INVENTION

The present invention relates to methods for reducing peroxide levels in non-polymeric preparations and to compositions used in and prepared by such methods.

BACKGROUND OF THE INVENTION

Sucrose acetate isobutyrate ("SAIB") is a hydrophobic liquid with limited water solubility. It is soluble in a large number of biocompatible solvents. SAIB has an unusual property—it undergoes a dramatic change in viscosity with small additions of heat or with the addition of solvents. It is a very viscous liquid, having a viscosity of approximately 3200 poise at 37° C. SAIB is produced by the controlled esterification of natural sugar (sucrose) with acetic and isobutyric anhydrides. SAIB metabolizes to sucrose, acetic acid and isobutyric acid.

SAIB is orally non-toxic and is currently used to stabilize emulsions in the food industry. In one example, SAIB is commonly found in the beverage industry, where it is used as a weighting agent to help stabilize the final beverage formula. Also, SAIB has been reported to be useful as a gelling system-type drug excipient that allows for sustained or controlled release of drugs. When in solution or in an emulsion, SAIB can be applied via injection or an aerosol spray. SAIB is compatible with cellulose esters and other polymers that can affect the rate of delivery of the substance. In one example, SAIB is the main ingredient for the SABER drug delivery system, which also consists of a pharmaceutically acceptable solvent.

Drug delivery systems, including SAIB delivery systems, are still confronted by various issues of drug instability, as such systems are considered for longer and longer drug delivery durations. Drug instability can occur via a number of factors, including denaturation, precipitation, oxidation, aggregation, and others. In particular, a number of excipients used to facilitate delivery and release of drugs have peroxides or are susceptible to the formation of peroxides, which may lead to oxidation of active ingredient in the formulation. In the example of SAIB, the presence of peroxides is deleterious to a drug incorporated in an SAIB drug formulation as the drug is likely to undergo oxidative degradation. Thus, in order to formulate any drug formulation based on SAIB that provides enough of a stable environment to facilitate the delivery of a drug, the peroxide levels must be reduced.

There is no known process for removal of peroxides from SAIB at present, despite availability of processes for the removal of peroxides from other materials such as polymers. Therefore, there still remains a need for a drug formulation of SAIB having improved properties to reduce the degradation of the drug therein.

SUMMARY OF THE INVENTION

An aspect of the present invention comprises methods of treating sucrose acetate isobutyrate (SAIB) formulations to be used as drug delivery vehicles comprising adding to the formulations an amount of bisulfite salt effective to substantially remove peroxides, the bisulfite salt comprising sodium metabisulfite, potassium metabisulfite, sodium bisulfite, or potassium bisulfite, or a mixture thereof.

In another aspect of the present invention, provided are drug delivery vehicles adapted to provide prolonged stability of a drug that is to be delivered in vivo comprising sucrose acetate isobutyrate having substantially reduced levels of peroxide, the drug delivery vehicle being treated with an amount of bisulfite salt effective to substantially reduce levels of peroxide in said drug delivery vehicle, the bisulfite salt comprising sodium metabisulfite, potassium metabisulfite, sodium bisulfite, or potassium bisulfite, or a combination thereof.

BRIEF DESCRIPTION OF THE DRAWINGS

The invention is illustrated by way of example and is not intended to be limited by the accompanying figures.

FIG. 1 illustrates a bar graph of the results of Study I—Stability of omega-interferon in untreated SAIB.

FIG. 2 illustrates a bar graph of the results of Study IIa—Stability of omega-interferon in alumina treated SAIB.

FIG. 3 illustrates a bar graph of the results of Study IIb—Stability of omega-interferon in alumina treated SAIB.

FIG. 4 illustrates a bar graph of the results of Study III—Stability of omega-interferon in untreated SAIB.

FIG. 5 illustrates a bar graph of the results of Study VIb—Stability of omega-interferon in untreated SAIB.

FIG. 6 illustrates a bar graph of the results of Study VIa—Stability of omega-interferon in sodium metabisulfite treated SAIB.

FIG. 7 illustrates a bar graph that provides comparisons of oxidation of omega-IFN in sodium metabisulfite treated and untreated SAIB.

DETAILED DESCRIPTION OF ILLUSTRATIVE EMBODIMENTS

Figure 8:
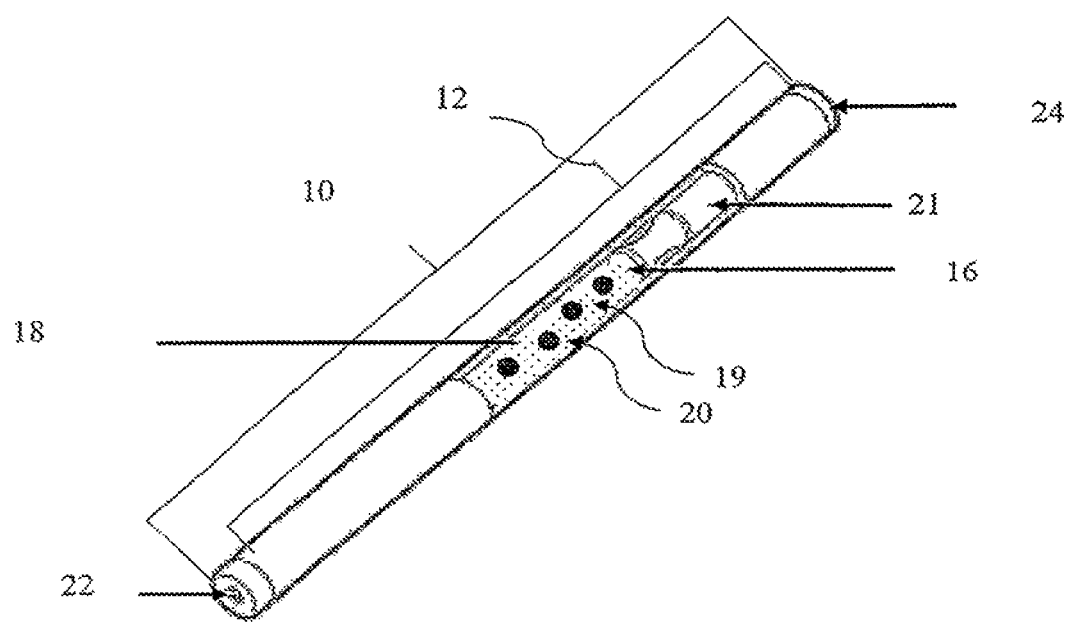
FIG. 8 illustrates an osmotically pump-driven implantable device, Duros® being an example, that facilitates in vivo delivery of an active agent in an SAIB vehicle.

In an aspect of the present invention, provided are methods of treating sucrose acetate isobutyrate formulations (SAID) that are to be used as drug delivery vehicles comprising adding an amount of a bisulfite salt effective for substantially removing peroxide from the formulations, the bisulfite salt comprising sodium metabisulfite, potassium metabisulfite, sodium bisulfite, or potassium bisulfite, or a combination thereof. Preferably, the bisulfite salt is sodium metabisulfite. A ratio ranging from about 1:1 to about 1:4 (weight:volume) SAIB:aqueous solution of bisulfite salt ("aqueous bisulfite salt") can be used. Preferably, the bisulfite salt is a metabisulfite salt. In some embodiments, the bisulfite salt is preferably sodium metabisulfite. Preferably, the ratio of the aqueous bisulfite salt to SAIB is 1:1. In one example, to purify 1 kg of SAID, a volume of sodium metabisulfite solution can be made up to 1 liter, and an approximate proportion of 1:1 of SAIB:aqueous sodium metabisulfite was used. The aqueous bisulfite salt in SAID can be from about 0.1% weight to volume of water (w/v) to about 50% w/v; preferably, from about 0.5% w/v to about 30% w/v. In some embodiments, the aqueous bisulfite salt is preferably from about 1% w/v to about 15% w/v. In some embodiments, the aqueous bisulfite salt is about 5% w/v solution in water.

The method removes peroxide to a level that is at least less than 50% of the levels before the method, or starting levels, and, preferably, less than 20% of the starting levels. In some embodiments, peroxide is removed to less than 10% of the starting levels. While in some embodiments, the method removes peroxide to a level that is less than 5% of the starting levels. Furthermore, the method can remove peroxide so that the resulting SAIB formulation contains peroxide in amounts less than 20 ppm, and, preferably, less than 10 ppm. In some embodiments, the method removes peroxide to result in an SAIB formulation containing less than 5 ppm. In some embodiments, the resulting SAIB formulation from this method can serve as a drug delivery vehicle for use with a medical delivery device, including a drug eluting stent, a catheter, or other drug delivery implants. In one example, the SAIB formulation can be loaded into an osmotically pump-driven implantable device of the type disclosed in U.S. Pat. No. 6,395,292, for example. Preferably, the osmotically pump-driven implantable device is a Duros® device (Alza Corporation, Mountain View, Calif.). In other embodiments, the SAIB formulation can serve as a drug depot for drug delivery.

In some embodiments, the step of adding the bisulfite salt comprises mixing a solution of the bisulfite salt with the sucrose acetate isobutyrate formulation. The SAIB formulation can be further comprised of a cosolvent, which can be selected from a number of solvents including pharmaceutically acceptable solvents, e.g., hexane, ethyl acetate, ethanol, benzyl benzoate, N-methyl pyrrolidone, and iso-propyl alcohol, among others. Preferably, the cosolvent is hexane or ethyl acetate. In some embodiments, the methods further comprise vacuum treating the formulation to remove the cosolvent. Also, some embodiments comprise the additional step of removing bisulfite salt from the formulation. This removal step comprises washing the formulation with water to remove the bisulfite salt. In the embodiments that incorporate the washing step, a further step of drying the formulation over magnesium sulfate can be utilized to remove the water. Alternatively, calcium chloride anhydrous, calcium sulfate anhydrous, activated silica gel, phosphorous pentoxide, or drying under vacuum, or a combination thereof can be used to also remove the water. In alternative embodiments, glycerin can be used to wash the bisulfite-added formulation to remove the bisulfite salt. Afterwards, residual glycerin can be removed by washing with water and then drying to remove water.

In some aspects of the present invention, the methods of substantially removing peroxide from a sucrose acetate isobutyrate formulation (SAW) comprising the steps of adding the aqueous bisulfite salt, washing the formulation, and drying the formulation are repeated at least once. The steps can be repeated to further reduce the levels of peroxide in the SAIB formulation.

In another aspect, the present invention includes a drug delivery vehicle comprising SAW that provides for prolonged stability of a drug that is to be delivered by maintaining substantially reduced levels of peroxide, the drug delivery vehicle being treated with sodium metabisulfite. The prolonged stability comprises reduced oxidation, deamidation, or aggregation, e.g., dimerization, of the drug over extended periods of time in which drug is within environment of delivery vehicle. Preferably the prolonged stability is reduced oxidation. The extended periods of time can be periods from about one week to a few months, and up to about a year. Preferably, the prolonged stability is evidenced by significant improvements in oxidation, deamidation, or aggregation levels of the drug when the delivery vehicle has been treated with a bisulfite salt versus untreated delivery vehicle. In some preferred embodiments, the prolonged stability is characterized as about 50% less oxidation, about 33% less deamidation, or about 75% less dimerization as compared to untreated delivery vehicles. The drug can be selected from any known and desired biomolecular material that can act as therapeutics and other therapeutic active agents that are susceptible to oxidative degradation. As it is used herein, the term "biomolecular material" refers to peptides, polypeptides, proteins, nucleic acids, viruses, antibodies, small molecules susceptible to oxidation, and any other naturally derived, synthetically produced, or recombinantly produced active agent that includes nucleic or amino acid. In some embodiments, for example, drugs can be selected from among the following: a steroid, MAIDS, peptides, proteins such as growth factors or hormones, anti-tumor agents, antibiotics, analgesics, local anesthetics, antiviral agents, antipsychotics, anticoagulants, oligonucleotides for gene therapy, active small molecules, and others.

As used herein, the term "removing" and all variations thereof, refer to decreasing by any measurable degree the level of peroxide present in a drug formulation. The term "substantially removing" is used herein to describe a dramatic decrease in the level of peroxide present in a drug formulation, such as SAW formulation. The dramatic decrease is at least 50% of original levels (levels before treatment) and in some instances is 10% of original levels. In preferred aspects of the present invention, the "substantial removal" describes a decrease to less than 5% of original levels.

As used herein, the term "drug delivery vehicle" or "delivery vehicle" refers to a formulation that is biocompatible and used to carry a drug without reacting with the same drug. Also, the vehicle does not alter or minimally alters the activity of the drug. Furthermore, the vehicle allows for the transport of the drug in vivo and eventual delivery of the drug to a biological site for therapeutic effect.

As used herein, the term "prolonged stability" is used to refer to the stabilizing effect of the drug delivery vehicles of the present invention on the carried drug. Prolonged stability can be evidenced by significant improvements in oxidation, deamidation, or aggregation of the drug over extended periods of time.

EXAMPLES

Different approaches were investigated for removal of peroxides from SA113, as indicated in Table 1.
Preparation of Suspension Each of the experiments involved protein particles consisting of omega-interferon, which were suspended in SAIB at a particle loading of either 4% or 10% by weight. The suspensions were prepared in a dry box under nitrogen at 45° C. The suspension was mixed for 15 minutes while maintaining the temperature. Suspension mixing was performed by hand. Aliquots from the prepared suspensions were transferred to clear crimp-top glass vials and sealed under nitrogen. Each aliquot contained at least six milligrams of protein to allow for stability testing in triplicate. These samples were stored in an oven at 40° C. Samples were withdrawn at regular intervals (as indicated in Table 1) and analyzed for omega-interferon content and purity was assessed using reverse phase I-IPLC and size exclusion chromatography.
Size Exclusion Chromatography Size exclusion chromatography (SEC) was used to monitor the omega-interferon content and purity in the formulations. The percentages of monomer and dimer in the formulation were quantified using SEC. The stability of omega-interferon was judged by using a stability indicating chromatographic technique based on reverse phase HPLC (rp-HPLC). This technique was used to monitor the oxidation, deamidation and formation of an unknown species of omega-interferon in the formulations. The peroxide content of the vehicle was determined using EP 2002, 2.5.5 (Method A with auto titration), See *Extra Pharmacopoeia,* 2002 Ed. Content and purity assay of omega-interferon by size exclusion chromatography (SEC).

Reverse Phase High Performance Liquid Chromatography
Purity assay and identity of omega-interferon recombinant in suspension systems by reverse phase high performance liquid chromatography (rp-HPLC).

The stability of omega-interferon was monitored in two different lots of untreated SAIB (as received) and in treated SAID (removal of peroxides), when treatment was applied. The studies are outlined below:

Study I: Stability in untreated SAIB (lot #TD1030507) for 2 weeks

Study IIa: Treatment of SAIB (lot #TD1030507) with neutral alumina by heating and stability in this treated SAIB for 4 weeks Study Treatment of SAIB (lot #TD1030507) with neutral alumina in presence of ethanol and stability in this treated SAIB for 4 weeks Study III: Stability in untreated SAIB (lot #TD2032663) for 2 weeks Study IV: Treatment of SAIB (lot #TD2032663) with basic alumina by heating Study V: Treatment of SAIB (lot #TD2032663) with 10% aqueous methionine solution by heating Study VIa: Treatment of SAIB (lot #TD2032663) with 5% aqueous solution of sodium metabisulfite and stability in treated SAIB for 8 weeks Study VIb: Stability in untreated SAIB (lot #TD2032663) for 8 weeks

TABLE 1

Details about stability studies of omega-interferon in SAIB

| Study # | SALB (Lot #) | Treatment | Particle loading | Time points | Tests |
|---|---|---|---|---|---|
| I | TD1030507 | Untreated | 4% | 0, 4, 7, 14 days | SEC, RP-HPLC |
| IIa | TD1030507 | Treated with neutral alumina by heating | 10% | 0, 2, 4 weeks | SEC, RP-HPLC |
| IIb | TD1030507 | Treated with neutral alumina using ethanol | 10% | 0, 2, 4 weeks | SEC, RP-HPLC |
| III | TD2032663 | Untreated | 10% | 0, 1, 2 weeks | SEC, RP-HPLC |
| IV | TD2032663 | Treated with basic alumina by heating | NA | NA | NA |
| V | TD2032663 | Treated with 10% aqueous solution of methionine | NA | NA | NA |
| VIa | TD2032663 | Treated with hexane and sodium metabisulfite | 10% | 0, 1, 2, 4, 8 weeks | SEC, RP-HPLC |
| VIb | TD2032663 | Untreated | 10% | 0, 1, 2, 4, 8 weeks | SEC, RP-HPLC |

Materials and Equipment

The following tables, Table 2 and Table 3, provide a list of materials and equipment that can be utilized to perform the experiments described, below.

TABLE 2

| List of materials<br>Materials |
|---|
| Spray dried omega-interferon particles |
| SAM, Eastman Chemical Company |
| Aluminum oxide (Powder) |
| Ethanol, absolute, 200 proof, AAPER |
| Aluminum oxide, basic, standard activity I, 50-200 μm, Sorbent Technologies |
| Aluminum oxide, basic, Super I, 50-200 μm, Sorbent Technologies |
| Methionine, USP, Ph Eur, JP |

TABLE 3

| List of equipment<br>Equipment |
|---|
| Branson Ultrasonic Cleaner Model 2510 |
| VAC Dry Box |
| Mettler AT261 Delta Range Balance |
| Mettler P33000 Balance |
| Sartorius Genius Electronic Analytical Balance |
| Hot plate |
| Oven (40° C.) |
| Millipore filter, white hydrophilic, Durapore Disc, SLVP, 25 mm, 5 μm |
| PTFE membrane filter, 0.2 μm, Titan filtration systems |

Example 1

Study I: Stability in Untreated SAIB (lot #TD1030507) for 2 Weeks

TABLE 4

Stability of omega-interferon in untreated SAIB (lot #: 1030507)—Study 1

| | Analysis by RP-HPLC (n = 3)** | | | |
|---|---|---|---|---|
| | Initial (t = 0) (AR 48452) (protein particles)*** | 4 days AR48424 | 7 days AR48562 | 14 days AR48450 |
| Assay (%) | NA | 0.59* (0.02) | 0.72 (0.00) | 0.68 (0.00) |
| % omega-IFN Purity | 93.37 (0.40) | 89.06 (0.46) | 87.65 (0.06) | 87.67 (0.26) |
| % Oxidized | 2.8 (0.71) | 7.21 (0.88) | 7.79 (1.09) | 8.31 (0.10) |
| % Deamidated | 0.8 (0.02) | 1.21 (0.00) | 1.28 (0.01) | 1.63 (0.03) |
| % Unknown | 3.03 (0.62) | 2.25 (0.66) | 3.27 (0.79) | 2.39 (0.38) |
| | Analysis by SEC (n = 3)** | | | |
| | Initial (AR 48452) (protein particles)*** | 4 days AR48424 | 7 days AR48562 | 14 days AR48450 |
| % Monomer | 100.00 (0.00) | 99.96 (0.01) | 99.60 (0.02) | 99.40 (0.00) |
| % Dimer | ND | 0.04 (0.00) | 0.38 (0.01) | 0.58 (0.02) |
| Unknown | ND | ND | 0.01 (0.00) | 0.01 (0.01) |

ND = Not detected,

*sampled by scraping container walls, so values might not be representative of the bulk

**standard deviation in parenthesis;

***protein particles − t = 0 for suspension

The preliminary stability study of omega interferon in untreated SAIB (lot #TD1030507, peroxide value—71.4 ppm) was over 2 weeks. The results indicated that up to 8.31% of omega-interferon was oxidized in two weeks, which corresponds to an increase of 5.51% with respect to particles (2.8% oxidation at t=0). See Table 4, FIG. 1. Furthermore, a small increase occurred in the percentage of deamidated form (+0.83%) of omega-interferon and the dimer (+0.58%). The high level of oxidation can be attributed to the high peroxide content of SAIB.

Example 2

Study IIa and IIb: Stability of SAIB (lot #TD1030507) Treated with Neutral Alumina with Heating or Neutral Alumina in Presence of Ethanol for 4 Weeks Treatment of SAIB with Neutral Alumina with Heating SAIB was heated to 75° C. Alumina (15% w/w) was added to the heated SAW. The mixture was stirred for 40 minutes and filtered though a 5.0 μm filter at 75° C. The treated SAIB was then collected, sampled for peroxide testing, and used for preparation of suspension for stability testing.

Treatment of SAIB with Neutral Alumina in Presence of Ethanol

SAIB was mixed with 15% absolute ethanol to reduce the viscosity. Basic alumina (15% w/w) was added to the SAIB containing ethanol. The resulting mixture was stirred for 1 hour and filtered though a 0.2 μm filter. The filtered SAIB was placed overnight under vacuum at 60° C. to remove the ethanol. This treated SAIB was then collected, sampled for peroxide testing, and used for preparation of suspension for stability testing.

TABLE 5

Stability of omega-interferon in alumina treated SAIB ((lot #: 1030507)—Studies IIa and IIb

|  | Initial (t = 0) (protein particles) | Initial (t = 0) AR 48570 | 2 weeks AR 48572 | 1 month AR 48565 |
|---|---|---|---|---|
| SAIB treated with neutral alumina by heating—Study IIa | | | | |
| Analysis by RP-HPLC (n = 3)** | | | | |
| Assay (%) | NA | 1.68 (0.01) | 1.70 (0.00) | 1.72 (0.01) |
| % omega-IFN Purity | 89.08 (0.56) | 87.56 (0.47) | 83.90 (0.15) | 82.97 (0.50) |
| % Oxidized | 1.72 (0.12) | 3.45 (0.06) | 6.85 (0.14) | 7.39 (0.21) |
| % Deamidated | 1.49 (0.01) | 1.46 (0.03) | 1.84 (0.03) | 2.42 (0.05) |
| % Unknown | 7.70 (0.45) | 7.52 (0.45) | 7.41 (0.01) | 7.22 (0.46) |
| Analysis by SEC (n = 3)** | | | | |
| % Monomer | 100.00 (0.00) | 100.00 (0.00) | 99.89 (0.01) | 99.50 (0.02) |
| % Dimer | trace | 0.00 | 0.11 (0.01) | 0.50 (0.02) |
| Unknown | 0.00 | 0.00 | 0.00 | 0.00 |
| SAIB treated with neutral alumina using ethanol—Study IIb | | | | |
| Analysis by RP-HPLC (n = 3)** | | | | |
| Assay (%) | NA | 1.66 (0.02) | 1.70 (0.01) | 1.70 (0.00) |
| % omega-IFN Purity | 89.08 (0.56) | 88.12 (0.49) | 83.76 (0.09) | 82.65 (0.19) |
| % Oxidized | 1.72 (0.12) | 3.08 (0.07) | 6.98 (0.12) | 7.42 (0.10) |
| % Deamidated | 1.49 (0.01) | 1.47 (0.01) | 1.88 (0.02) | 2.45 (0.09) |
| % Unknown | 7.70 (0.45) | 7.32 (0.48) | 7.38 (0.02) | 7.48 (0.05) |
| Analysis by SEC (n = 3)** | | | | |
| % Monomer | 100.00 (0.00) | 100.00 (0.00) | 99.87 (0.01) | 99.43 (0.02) |
| % Dimer | trace | 0.00 | 0.13 (0.01) | 0.57 (0.02) |
| Unknown | 0.00 | 0.00 | 0.00 | 0.00 |

**standard deviation in parenthesis

The stability of omega-interferon in alumina treated SAIB was tested. After one month in the neutral alumina treated SAIB (Study IIa and IIb), oxidation of omega-interferon increased by about 5.7% for both IIa and IIb. This indicates that alumina treatment of SAIB did not improve the stability of omega-interferon in SAIB. See Table 5. In addition, this analysis is also reflected in the high peroxide content of alumina treated SAIB (66.3 and 62.9 ppm, respectively). Treatment with neutral alumina was not effective in decreasing peroxide content.

Example 3

Study III: Stability in Untreated SAIB (lot #TD2032663) for 2 Weeks

TABLE 6

Stability of omega-interferon in untreated SAIB ((lot #: 2032663)—Study III

|  | Initial (t = 0) (AR 48217) (protein particles) | Initial (t = 0) AR 49640 | 1 week AR 49644 | 2 weeks AR 49647 |
|---|---|---|---|---|
| Analysis by RP-HPLC (n = 3)** | | | | |
| Assay (%) | NA | 1.69 (0.01) | 1.70 (0.00) | 1.68 (0.01) |
| % omega-IFN Purity | 88.98 (0.09) | 88.21 (0.03) | 84.95 (0.58) | 83.71 (0.48) |
| % Oxidized | 1.63 (0.04) | 3.20 (0.03) | 6.39 (0.05) | 7.21 (0.10) |
| % Deamidated | 1.45 (0.01) | 1.66 (0.01) | 1.45 (0.40) | 1.84 (0.03) |
| % Unknown | 7.94 (0.12) | 6.93 (0.04) | 7.22 (0.45) | 7.24 (0.45) |
| Analysis by SEC (n = 3)** | | | | |
| % Monomer | 99.93 (0.01) | 99.83 (0.02) | 99.75 (0.01) | 99.51 (0.01) |
| % Dimer | 0.07 (0.01) | 0.17 (0.02) | 0.25 (0.01) | 0.49 (0.01) |
| Unknown | ND | ND | ND | ND |

ND = Not detected
*n = 6
**standard deviation in parenthesis

Stability of omega-interferon in untreated SAIB was again tested. The results of a two week stability study (Study III) of omega-interferon in SAIB (lot #TD 2032663) are comparable to studies I and II. See Table 6, FIG. 4. The amount of oxidation was found to have increased by 5.58%, while deamidation increased by 0.39% and dimerization increased by 0.42%.

Example 4

Study IV and V: Treatment of SAIB (lot #TD2032663) with Basic Alumina with Heating or with 10% Aqueous Methionine Solution Treatment of SAIB with Basic Alumina with Heating SAIB was heated to 90° C. Basic alumina (15% w/w) was added to the heated SAIB. Two different grades of alumina were used—Basic Super I and Basic Standard Activity I. The resulting mixture was stirred for 40 minutes. The mixture was then centrifuged at 4000 rpm while temperature was maintained at 75° C. After centrifugation, the supernatant was collected and sampled for peroxide analysis.

Treatment of SAIB with 10% Aqueous Solution of Methionine

One part of SAIB was vigorously agitated with 4 parts of 10% aqueous solution of methionine at 80° C. for 45 minutes using a magnetic stirrer. (Evaporated water was replenished as necessary) Afterwards, the methionine solution was decanted. SAIB was then washed with 4 parts of water by agitating for 15 minutes at 70°-80° C. This washing step was carried out three times. SAIB was placed overnight in vacuum oven at 70° C. to remove residual water, and, afterwards, was sampled for peroxide analysis.

The peroxide content of SAIB treated with basic alumina or with aqueous methionine solution was determined to be 1.09.3 and 95.7 respectively (Study IV and V), indicating that these approaches were not successful in the removal of peroxides. See FIG. 7.

Example 5

Study VIa and VIb: Stability of SAIB (lot #TD2032663) Treated with 5% Aqueous Solution of Sodium Metabisulfite or Untreated for 8 Weeks Treatment of SAIB with 5% Aqueous Solution of Sodium Metabisulfite in Presence of Hexane SAIB was dissolved in two parts of hexane. The resulting solution was treated with a 5% aqueous solution of sodium metabisulfite by vigorous shaking. The aqueous layer was removed and the SAIB layer was washed with water. The SAIB layer was dried with MgSO$_4$. Hexane was removed from SAIB by evaporation under vacuum at 50° C. The treated SAIB was sampled for peroxide analysis and used for preparation of suspension for stability testing.

TABLE 7

Stability of omega-interferon in untreated SAIB and treated SAIB - Study VIa and VIb
Stability of omega-IFN in Untreated SAIB (Lot: TD 2032663)

| | Initial (t = 0) Protein particles AR 48219 | Initial (t = 0) AR 48445 | 1 week AR48441 | 2 weeks AR 48440 | 4 weeks AR 50132 | 8 weeks AR 50161 |
|---|---|---|---|---|---|---|
| | Analysis by RP-HPLC (n = 3)** | | | | | |
| Assay (%) | 11.45 (0.24) | 1.00 (0.01) | 1.00 (0.01) | 1.00 (0.01) | 0.94 (0.01) | 0.94 (0.03) |
| % omega-IFN | 88.91 (0.39) | 87.29 (0.25) | 83.10 (0.08) | 81.62 | 80.17 | 79.35 |
| % Oxidized | 1.90 (0.39) | 3.38 (0.19) | 7.86 (0.14) | 8.54 (0.07) | 8.94 (0.08) | 8.86 (0.06) |
| % Deamidated | 2.02 (0.01) | 2.15 (0.03) | 2.24 (0.09) | 2.59 (0.15) | 3.33 (0.04) | 4.46 (0.07) |
| % Unknown | 7.17 (0.44) | 7.18 (0.47) | 6.80 (0.02) | 7.25 (0.36) | 7.55 (0.05) | 7.33 (0.47) |
| | Analysis by SEC (n = 3)** | | | | | |
| % Monomer | 99.67 (0.01) | 99.57 (0.02) | 99.16 (0.01) | 98.93 | 99.15 | 97.18 |
| % Dimer | 0.25 (0.01) | 0.31 (0.02) | 0.72 (0.01) | 1.01 (0.04) | 0.47 (0.05) | 2.53 (0.13) |
| Unknown | 0.08 (0.00) | 0.12 (0.01) | 0.12 (0.00) | 0.06 (0.00) | 0.38 (0.02) | 0.30 (0.05) |

Note:
The omega content in the suspension was 1.00% and not 1.66% because the particles contained 11.45% omega and the loading of particles in suspension was at 10%

Stability of omega-IFN in Treated SAIB (Lot: TD 2032663)

| | Initial (t = 0) Protein particles AR 48219 | Initial (t = 0) AR 48445 | 1 week AR48441 | 2 weeks AR 48440 | 4 weeks AR 50132 | 8 weeks AR 50161 |
|---|---|---|---|---|---|---|
| | Analysis by RP-HPLC (n = 3)** | | | | | |
| Assay (%) | 11.45 (0.24) | 1.17 (0.01) | 1.15 (0.00) | 1.16 (0.00) | 1.15 (0.00) | 1.14 (0.01) |
| % omega-IFN | 88.91 (0.39) | 88.11 (0.35) | 86.25 (0.41) | 85.83 | 85.41 | 84.52 |
| % Oxidized | 1.90 (0.39) | 2.69 (0.17) | 3.26 (0.07) | 3.46 (0.09) | 3.56 (0.05) | 4.16 (0.11) |
| % Deamidated | 2.02 (0.01) | 2.26 (0.04) | 2.81 (0.01) | 2.94 (0.04) | 3.21 (0.06) | 3.64 (0.06) |
| % Unknown | 7.17 (0.44) | 6.97 (0.39) | 7.68 (0.37) | 7.77 (0.38) | 7.81 (0.45) | 7.77 (0.55) |
| | Analysis by SEC (n = 3)** | | | | | |
| % Monomer | 99.67 (0.01) | 99.59 (0.02) | 99.34 (0.02) | 99.41 | 99.42 | 99.00 |
| % Dimer | 0.25 (0.01) | 0.35 (0.02) | 0.53 (0.02) | 0.54 (0.02) | 0.29 (0.01) | 0.94 (0.06) |
| Unknown | 0.08 (0.00) | 0.05 (0.00) | 0.13 (0.00) | 0.05 (0.01) | 0.29 (0.01) | 0.06 (0.01) |

Note:
The omega content in the suspension was 1.17% and not 1.66% because the particles contained 11.45% omega and the loading of particles in suspension was at 10%.
**standard deviation in parenthesis The stability study (Study VIa and VIb, Table 7, FIGS. 5-7) conducted in treated (5% aqueous solution of sodium metabisulfite) and untreated SAIB shows that oxidation levels are reduced at 8 weeks, along with the reduction of peroxide levels—4.16% in treated SAIB versus 8.86% in untreated. SAIB equivalent to a change of 2.26% and 6.96%, respectively, from t=0 values of the protein particles. (For all relative changes reported herein, the changes are based on differences between the percentage values, e.g., percent oxidation, at $t_n$ and t=0 of the particles as opposed to relative percent change from value at t=0). Deamidation increased by 2.44% and 1.62% in untreated and treated SAIB, respectively. Dimerization increased by 2.28% and 0.59% in untreated and treated SAIB %, respectively. The quantities of unknown did not change significantly over time, which indicates that the extent of oxidation, deamidation and dimerization in treated SAIB (low peroxide value of 2.6 ppm) was lower than in untreated material. This treatment decreased the peroxide content substantially.

TABLE 8

Peroxide content of SAIB

| Study # | SAIB (Lot #) | Treatment | Peroxide value (ppm)* | AR numbers |
|---|---|---|---|---|
| I | TD1030507 | Untreated | 71.4 | 48557 |
| IIa | TD1030507 | Treated with neutral alumina by heating | 66.3 | 48568 |
| IIb | TD1030507 | Treated with neutral alumina using ethanol | 62.9 | 48568 |
| III | TD2032663 | Untreated | 115.9 | 48581 |
| IV | TD2032663 | Treated with basic alumina by heating | 109.3 | 48581 |
| V | TD2032663 | Treated with 10% aqueous solution of methionine | 95.7 | 48446 |
| VIa | TD2032663 | Treated with hexane and sodium metabisulfite | 2.6 | 49648 |
| VIb | TD2032663 | Untreated | 115.9** | 48581 |

*oxidative activity equivalent to hydrogen peroxide (n = 1)
**peroxide content determined during Study III As shown in FIG. 7, along with data provided in Table 8, treatment with an aqueous solution of sodium metabisulfite was effective in significantly reducing peroxide levels from 115.9 ppm to 2.6 ppm—almost 45 times, or 45 fold decrease. In comparison, treatment with neutral alumina, either with heat or with ethanol, resulting in only a nominal change in peroxide levels—a 7% or 12% decrease, respectively. In addition, treatment with basic alumina with heat or 10% aqueous methionine only resulted in nominal change in peroxide levels—a 6% or 18% decrease, respectively.

FIG. 8 illustrates an osmotically pump-driven implantable device for delivering an SAIB formulation acting as a drug delivery vehicle, active agent within. Depicted in FIG. 8 is an osmotically pump-driven implantable device 10 shown comprising an impermeable reservoir 12. The reservoir 12 is divided into two chambers by a piston 16. The first chamber 18 is adapted to contain an SAIB formulation 19 containing an active agent 20 and the second chamber 21 is adapted to contain a fluid-imbibing agent. A back-diffusion regulating outlet 22 is inserted into the open end of the first chamber 18 and a semipermeable membrane 24 encloses the open end of the second chamber 1. The piston 16 is driven towards the open end of the first chamber 18 by the osmotic pressure generated by the fluid-imbibing agent in the second chamber 21. The pressure created by the piston 16 can force the contents of the first chamber 18 out the opening, i.e., the SAIB formulation 19 comprising active agents 20. The release rate of the active agent can be governed by the osmotic pumping rate.

It is to be appreciated that certain features of the invention which are, for clarity, described above in the context of separate embodiments, may also be provided in combination in a single embodiment. Conversely, various features of the invention that are, for brevity, described in the context of a single embodiment, may also be provided separately or in any subcombination. Further, reference to values stated in ranges includes each and every value within that range, unless clearly expressed otherwise.

The entire disclosure of each patent, patent application, and publication cited or described in this document is incorporated herein by reference.

We claim:

1. A formulation comprising:
   a drug;
   sucrose acetate isobutyrate; and
   peroxide,
   wherein the peroxide is present in the formulation at a level ranging from 2.6 ppm to 20 ppm.

2. The formulation of claim 1, wherein the peroxide is present in the formulation at a level ranging from 5 ppm to 20 ppm.

3. The formulation of claim 1, wherein the peroxide is present in the formulation at a level ranging from 10 ppm to 20 ppm.

4. The formulation of claim 1, wherein the peroxide is present in the formulation at a level ranging from 2.6 ppm to 10 ppm.

5. The formulation of claim 1, wherein the peroxide is present in the formulation at a level ranging from 5 ppm to 10 ppm.

6. The formulation of claim 1, wherein the drug is selected from peptides, polypeptides, proteins, nucleic acids, viruses, antibodies and small molecules susceptible to oxidation.

7. The formulation of claim 1, wherein the drug is selected from steroids, NSAIDs, growth factors, hormones, anti-tumor agents, antibiotics, analgesics, local anesthetics, antiviral agents, antipsychotics, anticoagulants, and oligonucleotides for gene therapy.

8. The formulation of claim 1, further comprising a pharmaceutically acceptable solvent.

9. The formulation of claim 1, further comprising a solvent comprising hexane, ethyl acetate, ethanol, benzyl benzoate, N-methyl pyrrolidone, or isopropyl alcohol, or a combination thereof.

10. The formulation of claim 1, further comprising N-methyl pyrrolidone.

11. The formulation of claim 1, wherein the drug comprises a local anesthetic and the formulation further comprises N-methyl pyrrolidone.

12. The formulation of claim 1, wherein the drug comprises a local anesthetic and the formulation further comprises a pharmaceutically acceptable solvent.

13. A formulation comprising:
    a drug;
    sucrose acetate isobutyrate; and
    peroxide,
    wherein the peroxide is present in the formulation at a level ranging from 2.6 ppm to 20 ppm, and
    wherein the formulation is polymer-free.

14. The formulation of claim 13, wherein the peroxide is present in the formulation at a level ranging from 5 ppm to 20 ppm.

15. The formulation of claim 13, wherein the peroxide is present in the formulation at a level ranging from 2.6 ppm to 10 ppm.

16. The formulation of claim 13, wherein the drug is selected from steroids, NSAIDs, growth factors, hormones, anti-tumor agents, antibiotics, analgesics, local anesthetics, antiviral agents, antipsychotics, anticoagulants, and oligonucleotides for gene therapy.

17. The formulation of claim 13, further comprising a pharmaceutically acceptable solvent.

18. The formulation of claim 13, further comprising N-methyl pyrrolidone.

19. The formulation of claim 13, wherein the drug comprises a local anesthetic and further comprising N-methyl pyrrolidone.

20. The formulation of claim 13, wherein the peroxide is present in the formulation at a level ranging from 5 ppm to 10 ppm.

21. The formulation of claim 13, wherein the drug is selected from peptides, polypeptides, proteins, nucleic acids, viruses, antibodies and small molecules susceptible to oxidation.

22. The formulation of claim 13, wherein the drug comprises a local anesthetic and the formulation further comprises a pharmaceutically acceptable solvent.

* * * * *

UNITED STATES PATENT AND TRADEMARK OFFICE
CERTIFICATE OF CORRECTION

PATENT NO. : 11,083,796 B2  
APPLICATION NO. : 16/542230  
DATED : August 10, 2021  
INVENTOR(S) : Gunjan Junnarkar et al.

Page 1 of 1

It is certified that error appears in the above-identified patent and that said Letters Patent is hereby corrected as shown below:

In the Specification

Column 2, Line 46, replace "(SAID)" with --SAIB--

Column 2, Line 62, replace "(SAID)" with --SAIB--

Column 3, Line 49, replace "SAW" with --SAIB--

Column 3, Line 55, replace "SAW" with --SAIB--

Column 4, Line 15, replace "MAIDS" with --NSAIDS--

Column 4, Line 25, replace "SAW" with --SAIB--

Column 4, Line 48, replace "SA113" with --SAIB--

Column 5, Line 19, replace "SAID" with --SAIB--

Column 7, Line 17, replace "SAW" with --SAIB--

Column 11, Line 42, replace "1" with --21--

Signed and Sealed this  
Twenty-first Day of September, 2021

Drew Hirshfeld  
*Performing the Functions and Duties of the*  
*Under Secretary of Commerce for Intellectual Property and*  
*Director of the United States Patent and Trademark Office*